United States Patent [19]

Rudnick

[11] Patent Number: 5,314,443
[45] Date of Patent: May 24, 1994

[54] PROSTATE BALLOON DILATATION CATHETER

[75] Inventor: James J. Rudnick, Plainfield, N.J.

[73] Assignee: Meadox Medicals, Inc., Oakland, N.J.

[21] Appl. No.: 7,048

[22] Filed: Jan. 21, 1993

Related U.S. Application Data

[63] Continuation of Ser. No. 542,869, Jun. 25, 1990, abandoned.

[51] Int. Cl.$^5$ .............................................. A61M 29/02
[52] U.S. Cl. ...................................... 606/192; 604/96
[58] Field of Search ...................... 604/96, 97, 98, 101, 604/192; 600/11; 606/191-196

[56] References Cited

U.S. PATENT DOCUMENTS

| | | |
|---|---|---|
| 550,238 | 11/1895 | Allen, Jr. . |
| 2,078,686 | 4/1937 | Rowe . |
| 2,642,874 | 6/1951 | Keeling . |
| 2,849,002 | 8/1958 | Oddo . |
| 2,936,760 | 5/1960 | Gants . |
| 3,977,408 | 8/1976 | MacKew . |
| 4,141,364 | 2/1979 | Schultze . |
| 4,205,691 | 6/1980 | Patel . |
| 4,219,026 | 8/1980 | Layton . |
| 4,311,146 | 1/1982 | Wonder . |
| 4,432,757 | 2/1984 | Davis, Jr. . |
| 4,575,371 | 3/1986 | Nordquist et al. ............... 604/96 |
| 4,660,560 | 4/1987 | Klein . |
| 4,737,142 | 4/1988 | Heckele ........................ 604/95 |
| 4,762,128 | 8/1988 | Rosenbluth . |
| 5,030,227 | 7/1991 | Rosenbluth et al. ............ 606/192 |
| 5,045,061 | 9/1991 | Seifert et al. .................. 604/96 |
| 5,103,804 | 4/1992 | Abele et al. ................... 128/4 |

FOREIGN PATENT DOCUMENTS 341998 of 0000 European Pat. Off. .
1566674 2/1978 United Kingdom .

OTHER PUBLICATIONS

Biomedical Business International, Jun. 20, 1989, Balloon Dilitation of the Prostate, vol. XII, No. 6, pp. 82-83.

Primary Examiner—C. Fred Rosenbaum
Assistant Examiner—Manuel Mendez
Attorney, Agent, or Firm—Michael I. Wolfson

[57] ABSTRACT

A direct vision prostate balloon catheter for treating benign prostate hyperplasia to dilate a prostate gland to reduce constriction of the urethra is provided. The catheter includes an expandable balloon and a sighting device such as a cystoscope telescopic lens proximal to the veru montanum to assist in properly positioning the expandable member. The balloon can have a thickened distal end and an overlapping proximal end to prevent undesirable migration during expansion. Alternatively, the balloon can be mounted on two tubes, one slidable axially inside the other to control balloon extension during expansion of the balloon. This construction provides advantages such as proper dilation of the prostatic urethra and helps prevent undesirable dilation of the external sphincter.

20 Claims, 4 Drawing Sheets

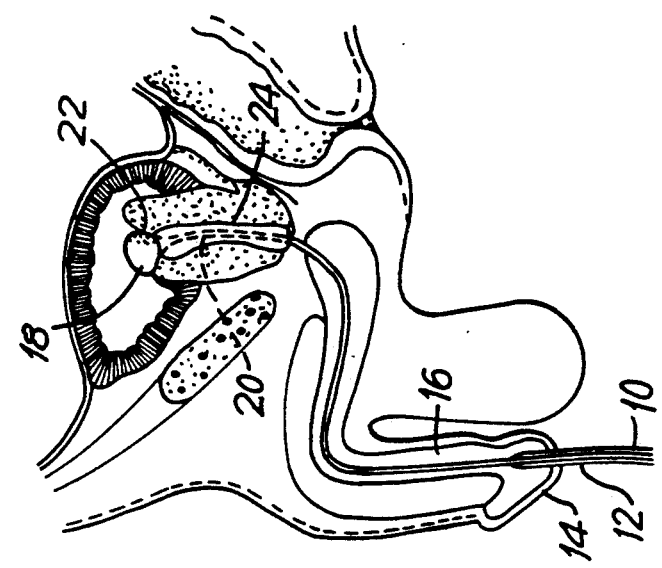
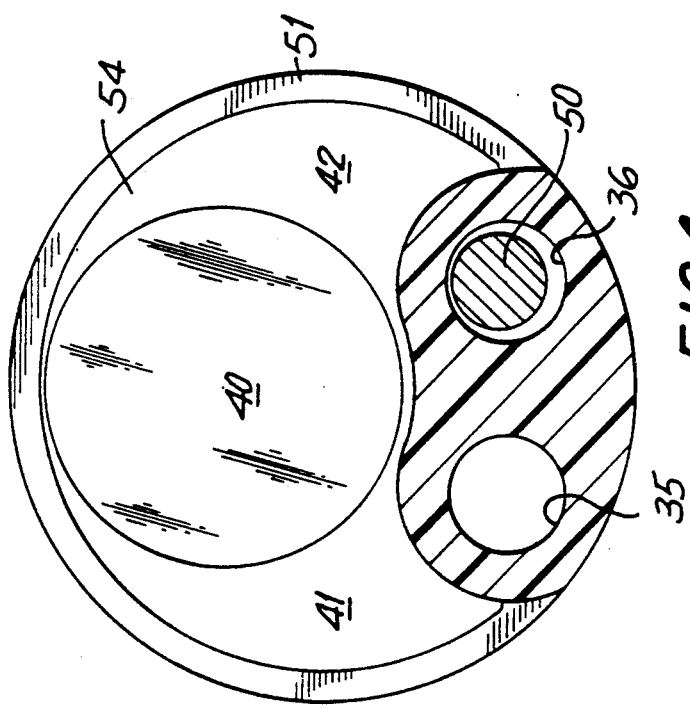
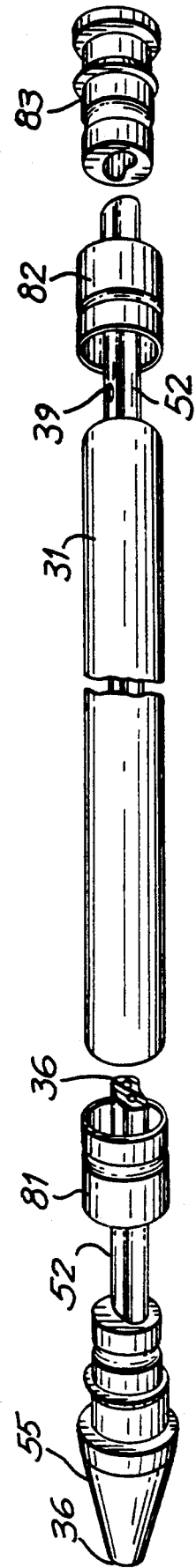
FIG.4
FIG.7

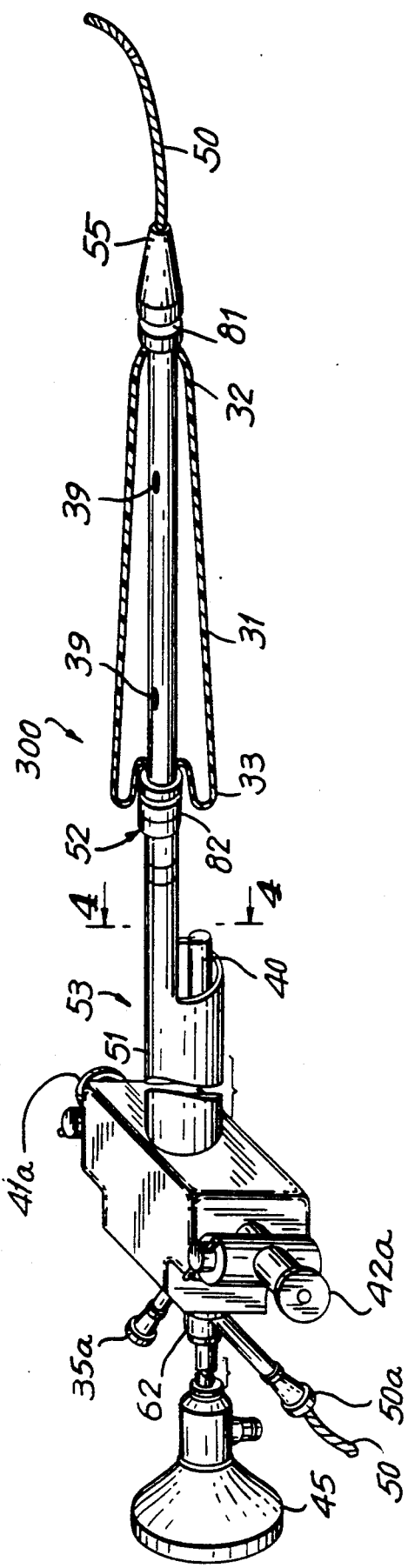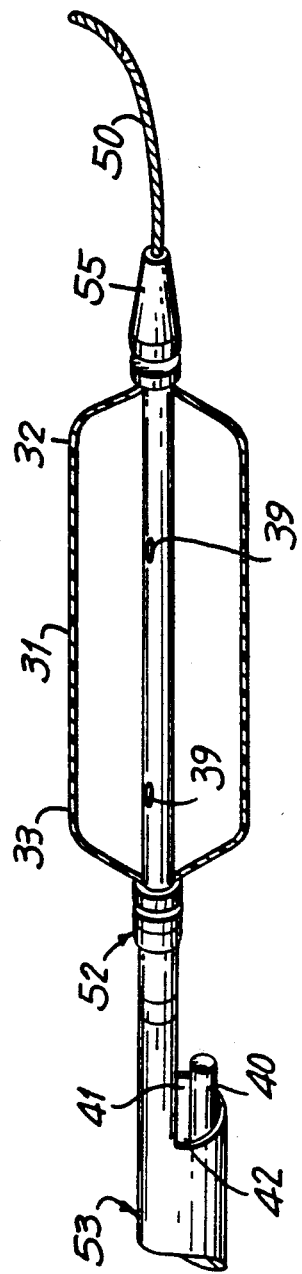

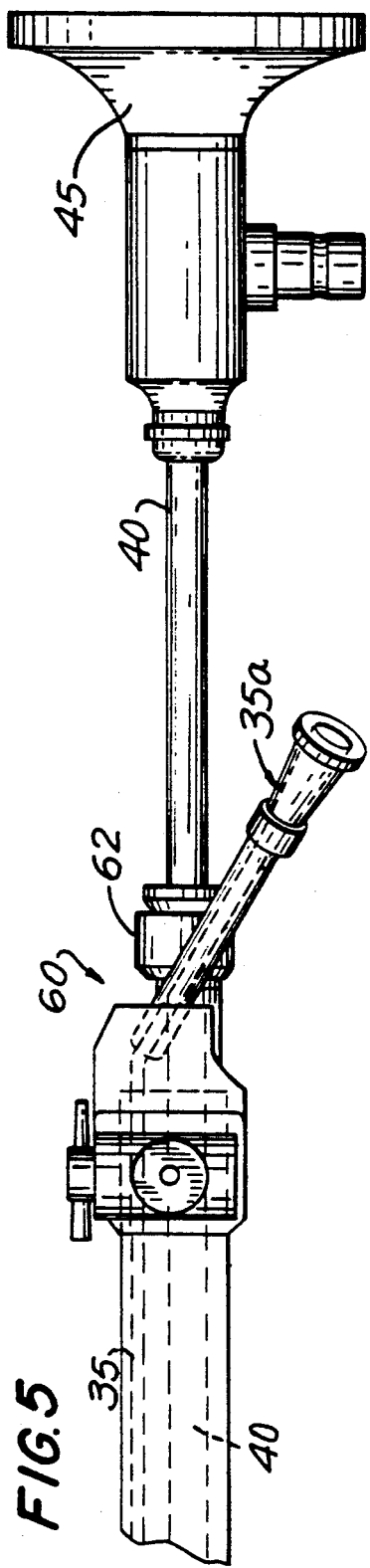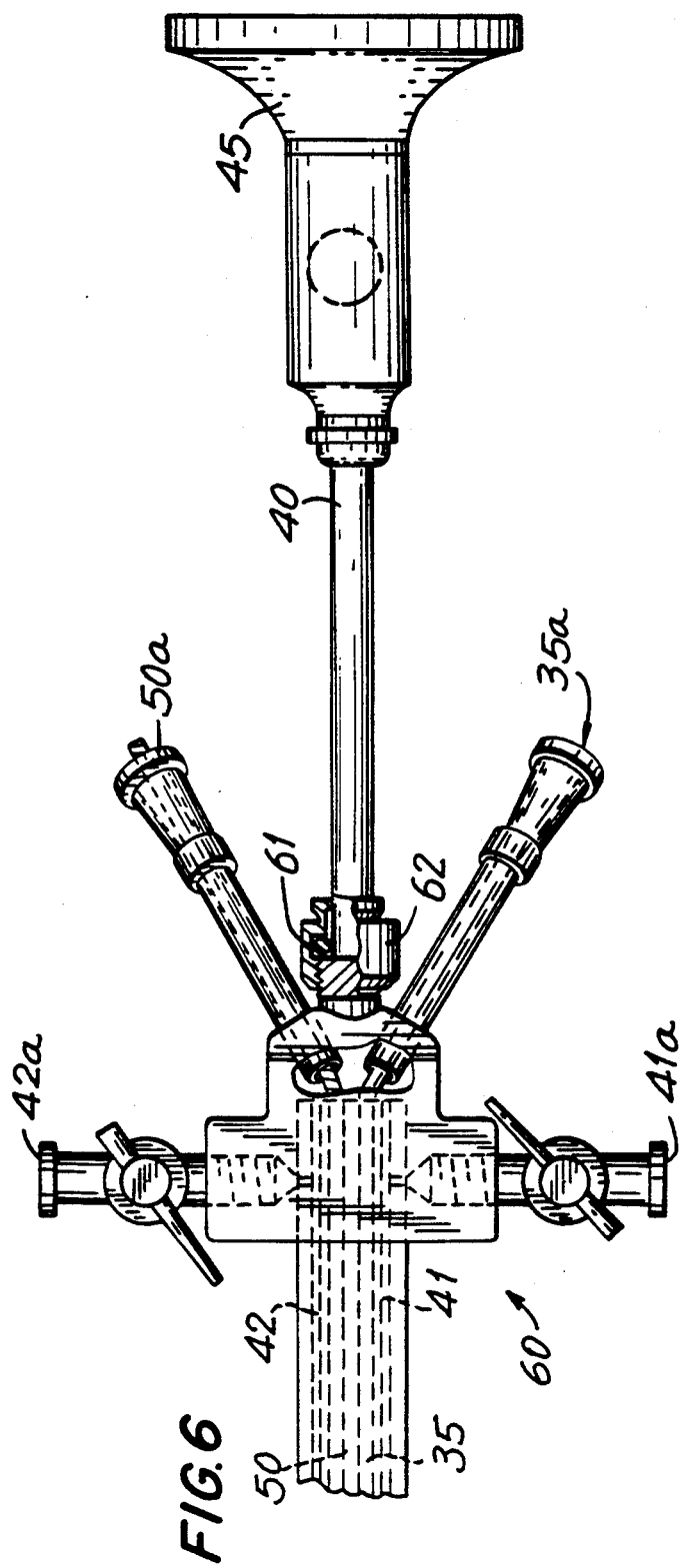

1

PROSTATE BALLOON DILATATION CATHETER

This is a continuation of application Ser. No. 07/542,869, filed Jun. 25, 1990 for PROSTATE BALLOON DILATATION CATHETER, and now abandoned.

BACKGROUND OF THE INVENTION

The invention relates generally to a device appropriate
surgical treatment of benign prostate hyperplasia and more particularly to a balloon catheter appropriate for dilating a portion of the urethra constricted by an enlarged prostate gland.

Benign prostate hyperplasia (BPH) is a disease characterized by enlargement of the prostate gland. As the prostate enlarges, it compresses the urethra, impairs urination and can lead to urinary tract infection and possible renal failure. Surgical and non-surgical treatment of BPH have been proposed.

Surgical treatment of BPH typically involves transurethral resection of the prostate. This procedure requires 5 to 6 days of hospitalization and is associated with some morbidity. Balloon dilation of the prostate is emerging as an important non-surgical near-term treatment for BPH. It can be carried out under sedation and local anesthesia in about 20 minutes. In this procedure a balloon catheter is inserted through the urethra to the prostate and the balloon is inflated to compress the internal tissue and stretch the outer capsule of the prostate. The patient can return home with a Foley catheter in place for two days. The recovery period is usually 3 to 4 days.

An example of a balloon apparatus for treating BPH is described in U.S. Pat. No. 4,660,560. FIG. 1 is a cross-sectional view of a dilating catheter assembly 10 positioned in the male urinary tract. A multi-channel cystoscope 12 is received through penile meatus 14 and is positioned in urethra 16 in which dilating catheter 10 is passed through one of its lumens. An extended Foley-balloon 18 is anchored to bladder neck 22 while an annular balloon 20 is fixedly positioned with respect to the prostatic urethra as defined by bladder neck 22 and veru montanum 24. Pressure dilation of the prostatic urethra by annular balloon 20 continues as long as it is deemed necessary. U.S. Pat. No. 4,762,128 discloses al single prostate balloon catheter for imparting an expanded tubular stent to extend long term patency. Catheters such as these are not fully satisfactory since they require multiple instrumentations of the urethra and multiple components such as a sighting lens, sheath and dilation catheter. These are awkward to simultaneously position properly at the prostate. Such catheters can lead to improper dilation of the external sphincter or improper dilation beyond the bladder neck. Furthermore, a 26 F plastic sheath, which is undesirably large, is required to insert and withdraw the balloon and a lens.

Another example of a balloon catheter for treating BPH is described in European patent application No. 0,341,988. A location or positioning balloon is located proximal to a prostate dilation balloon along the catheter. The location balloon is positioned to be at the bulbous urethra when the dilation balloon is at the prostate urethra. This fixes the location balloon to be intermediate the external sphincter and bladder to maintain the dilation balloon in proper position when it is inflated at the prostate urethra. The location balloon is sized to fit the bulbous urethra on inflation to prevent undesirable dilation of the external sphincter.

The catheter described in the European patent application also has drawbacks. To position the dilation balloon properly, a fluoroscope or lens is required. The fluoroscope exposes the patient to unnecessary radiation and the lens must be inserted unguided alongside the catheter shaft, increasing the likelihood of deleteriously scraping the urethra. Either option makes the entire procedure undesirably complex.

Balloons for prostate catheters are commonly substantially not elastic. Accordingly, when the conventional balloon is to be removed, it must first be threaded into a sheath. This makes the procedure and device unduly complicated.

Accordingly, it is desirable to provide an improved balloon catheter for dilating the prostate to reduce constriction of the urethra which overcomes the shortcomings of available prostate balloon catheters.

SUMMARY OF THE INVENTION

Generally speaking, in accordance with the invention, a direct vision catheter for dilating a prostate gland to reduce constriction of the urethra is provided. The catheter includes a catheter shaft with an expandable member such as a balloon and a sighting device such as a fiber optic lens to assist in properly positioning the expandable member. The catheter includes a first lumen to accept a telescope and can include a device to secure the telescope, to provide direct vision of the proximal end of the balloon and for maintaining proper balloon position during inflation. Additional lumens provide for rinsing the lens, balloon inflation and guide wire passage. The balloon is preferably elastic and of a self-wrapping construction mounted at the distal end of the catheter shaft. The balloon can be formed with a thickened distal end to limit expansion and prevent undesirable migration into the bladder during expansion. Alternatively, the balloon can be mounted to the ends of two slidable tubes to control balloon extension during inflation of the balloon.

Accordingly, it is an object of the invention to provide an improved catheter for dilatation of an enlarged prostate.

Another object of the invention is to provide an improved balloon catheter of reduced diameter for dilating an enlarged prostate.

A further object of the invention is to provide an improved balloon catheter for prostate dilatation that is less irritating to the urethra.

Still another object of the invention is to provide an improved balloon catheter that can dilate the prostate without adversely affecting the external sphincter of the bladder.

Still a further object of the invention is to provide a catheter with direct vision of the balloon and anatomical landmarks, e.g. the veru montanum and external sphincter, during insertion and inflation.

Still other objects and advantages of the invention will in part be obvious and will in part be apparent from the specification and drawings.

The invention accordingly comprises the features of construction, combination of elements, and arrangement of parts which will be exemplified in the constructions hereinafter set forth, and the scope of the invention will be indicated in the claims.

BRIEF DESCRIPTION OF THE DRAWINGS

FIG. 1 is a cross-sectional view of a conventional urethral dilating catheter inserted to the male urinary tract;

FIG. 2 is a perspective view of a balloon catheter with the balloon in the deflated condition constructed in accordance with the invention;

FIG. 3 is a partial perspective view of the distal end of the catheter of FIG. 2 with the balloon in an inflated condition;

FIG. 4 is a cross-sectional view of the catheter of FIG.@2 taken along line 4—4;

FIG. 5 is a partial side elevational view of the proximal end of a catheter constructed in accordance with the invention.

FIG. 6 is a top plan view of the proximal end of the catheter of FIG. 5;

FIG. 7 is a partial exploded view showing the separate elements of the distal end of the catheter of FIG. 2;

DESCRIPTION OF THE PREFERRED EMBODIMENTS

Figure 8:
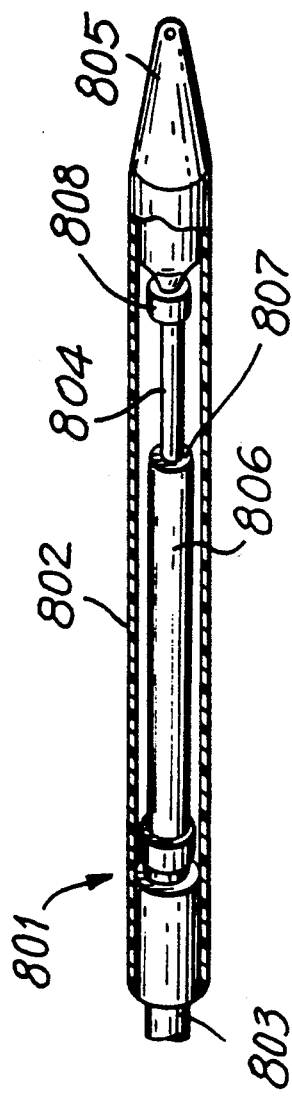
FIG. 8 is a partial side view of the distal end of a balloon catheter constructed in accordance with another embodiment of the invention.

A prostate balloon catheter 300 constructed in accordance with the invention is shown in FIG. 2. Catheter 300 includes an expandable dilation device such as an expandable bulb or balloon 31 mounted on a shaft 51. Balloon 31 is positioned in the urethra by threading shaft 51 along a guide wire 50 to a position determined by assistance from visual observation through a sighting device such as a telescope or a fiber optic lens 40 provided within a lumen in shaft 51. Balloons for balloon catheters and providing fluid to the distal end of a shaft for inflating the balloon are well known in the art.

Catheter 300 is advantageous due in part to the one piece, small diameter construction which permits proper positioning of balloon 31 without excessive irritation to the urethra or damage to the external sphincter of the bladder. It is advantageous to inflate balloon 31 to dilate the constricted prostatic urethra without dilating the external sphincter at the prostate apex. Accordingly, to effectively dilate the entire prostate length it is necessary to prevent balloon 31 from migrating into the bladder during inflation.

To aid in proper balloon position balloon 31 can be constructed with a thick wall balloon region 32 distal to a thin wall balloon region 33. Thick wall region 32 is at the leading end of catheter 300 and is positioned in and through the bladder neck. In the deflated condition, thin wall region 33 is layered over itself so that during inflation, balloon 31 will primarily expand radially and will not be displaced longitudinally to exert undesirable forces or reposition balloon 31 within an improper portion of the urethra. Thick wall balloon region 32 retards inflation of the distal end of balloon 31 which significantly retards migration of balloon 31 through the bladder neck into the bladder. Accordingly, during inflation, balloon 31 substantially maintains its position in the prostate to prevent undesirable injury to the external sphincter muscle and to properly dilate the entire prostrate.

Balloon 31 should inflate to be about 35 mm or at least about 30 mm and should be available in lengths from about 15 to 55 mm to accommodate various prostate urethra lengths. Balloon 31 should be elastic and able to hold about 6 to 8 atm until maximum volume, for at least three to four 10 minute cycles. Preferably, balloon 31 has a polymer fiber/polyurethane, a glass fiber/silicone or a carbon fiber/latex construction to provide desirable strength and expansion characteristics. On deflation, balloon 31 should return substantially to its pre-expansion shape and position.

Shaft 51 should be smooth and rigid enough for proper insertion without the need to utilize a cystoscope or outer sheath. FIG. 4 shows a cross-section of catheter 300 taken along line 4—4 of FIG. 2. Shaft 51 includes three separate lumens. As shown in FIG. 3, shaft 51 includes a dilation portion 52 of reduced cross-section at the distal end and a viewing portion 53 proximal to dilatation portion 52. A guide-wire lumen 36 extends through catheter shaft 51 from the proximal end to the distal tip of shaft 51. The overall diameter of shaft 51 should be less than 26 F, and more preferably from about 23.5 to 21 F, or thinner.

Viewing portion 53 of shaft 51 encloses a crescent shaped lumen 54. Lens 40 slides through lumen 54. When lens 40 is in place, it divides lumen 54 into two rinsing lumens 41 and 42 which are in fluid communication with a pair of rinsing ports 41a and 42a, respectively at the proximal end of shaft 51. One of rinsing lumens 41 and 42 provides rinsing fluid to lens 40 to improve the ability to see through fiber optic lens 40. The other rinsing lumen can act as a drain for the rinsing fluid. Dilation portion 52 is distal to viewing portion 53 and encloses guide wire 50 and an inflation lumen 35. Inflation lumen 35 is in fluid communication with an inflation port 35a to provide fluid for inflating balloon 31 through a pair of holes 39 in the shaft wall.

FIG. 7 shows the individual components of the distal end of catheter 300. A molded tip 55 of dilation portion 52 is formed with guide wire lumen 36 and seals off inflation lumen 35. Tip 55 is tapered and rounded to avoid irritation to the urethra during insertion. Preferably a pair of radio-opaque marker bands 81 and 82 seal the balloon ends and prevent exposed rough edges. The tip must be constructed to not be deformed by the radio-opaque bands. Binding, welding, gluing or other process could also be used for balloon attachment. A molded spacer 83 is disposed between marker band 82 and shaft 51. It is preferable to provide spacer 83 with a bright color to aid in visual positioning of balloon 31.

Referring to FIGS. 5 and 6, a connector 60 is coupled to the proximal end of catheter 300 and includes a pair of rinsing ports 41a and 42b in fluid communication with rinsing lumens 41 and 42, respectively to provide fluid for rinsing lens 40. Connector 60 also includes a guide wire port 50a for insertion of guide wire 50 and a balloon inflation port 35a, operatively coupled to inflation lumen 35 for providing fluid for inflating balloon 31 through holes 39.

Figure 9:
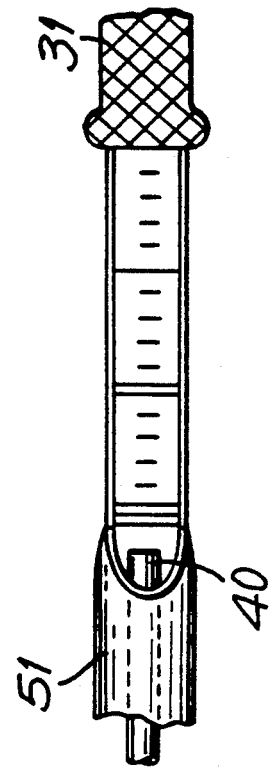
FIG. 9 is a bottom plan view of the distal end of a balloon catheter constructed in accordance with the invention.

Connector 60 can accept many commercially available cystoscopic telescope lens for viewing balloon 31. During insertion of balloon 31, the physician pears into eye piece 45 and through the telescope lens 40 to insure that balloon 31 is in proper position prior to inflation. As shown in FIG. 3, lens 40 is offset and at the bottom of shaft 51. Thus, balloon 31 does not obstruct the view of anatomical landmarks through lens 40 when it is in a deflated condition. As shown in FIG. 9, shaft 52 can be provided with graduations to assist in proper positioning. When the user looks into eye piece 45 through lens 40, balloon 31 can be properly positioned and then inflated to dilate the prostate without injuring the external sphincter. A device for clamping telescope lens 40 in position relative to shaft 51 is provided by compression of an elastomer ring 61 by tightening a threaded cap 62.

In another embodiment, as shown in FIG. 8, a catheter 801 including a dilation bulb 802 may be mounted on the distal end of a catheter shaft 803 as described by Hanecka and Olbert in U.K. Patent No. 1,566,674. As shown in FIG. 8, catheter 801 includes a tip 805 constructed as tip 55 of FIG. 2. Catheter 801 includes an inner tube 804 slidable within an outer tube 806 having a distal end 807. Tubular elastic expandable balloon 802 is sealingly mounted to tubes 802 and 806 with the distal end of balloon 802 sealingly attached to inner tube 804 and the proximal end of balloon 802 attached to outer tube 806. When balloon 802 is inflated, inner tube 804 retracts into outer tube 806 with a stop 808 at the distal end of inner tube 804 at tip 805 contacting distal end 807 of outer tube 806. Catheter 801 presents advantageous features because it permits control of bulb elongation and displacement during inflation by selectively sliding inner tube 804 within outer tube 806 to control length and position of balloon 802.

Balloons 31 and 802 may be formed of typical balloon catheter materials, such as polyester, polyethylene, urethane or silicone based materials. It should be of an elastic material which can be inflated to a diameter of about 30 mm and be about 15 to 60 mm in length. Preferably, it will deflate rapidly and hold about 6 to 8 atmospheres of pressure for a minimum of 3 to 4 cycles of 10 minutes duration. Typically, such materials are polyurethane elastomers with polyester, nylon, or aramid reinforcements; silicone resin with reinforcements such as glass or nylon fibers; and latex material with a carbon fiber reinforcement.

It will thus be seen that the objects set forth above, among those made apparent from the preceding description, are efficiently attained and, since certain changes may be made in carrying out the above method without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A prostate balloon dilatation catheter for treating benign prostate hyperplasia, comprising:
   an elongated flexible shaft having a longitudinal axis, which is flexible along its entire length, having a proximal end and a distal end and at least two lumens therethrough, the first lumen denominated an inflation lumen and the second lumen denominated a viewing lumen;
   the inflation lumen within the shaft extending from the proximal end of the catheter shaft to the distal region of the shaft;
   a balloon portion mounted at the distal region of the shaft in communication with the inflation lumen for expanding the balloon to dilate the prostate;
   the viewing lumen within the flexible shaft extending from the proximal end to a position proximal to the balloon portion for receiving viewing means for permitting an operator to view the proximal portion of the balloon and anatomical landmarks to accurately dilate the prostate without injury to the external sphincter when the balloon is expanded.

2. The balloon catheter of claim 1, further including a lumen for receiving a guide wire for assisting in inserting the catheter.

3. The balloon catheter of claim 1, including lumen means for rinsing the viewing means.

4. The balloon catheter of claim 1, wherein the viewing lumen is radially offset from the axis of the catheter shaft and includes viewing means in the viewing lumen, the viewing means being a cystoscope telescopic lens.

5. The balloon catheter of claim 4, wherein the shaft includes a third lumen extending from the proximal end of the flexible shaft to the distal end thereof for receiving a guide wire, the flexible shaft adapted to be displaced along a guidewire installed in the guidewire lumen.

6. The balloon catheter of claim 5, wherein the balloon is a flexible expandable member having a distal end and a proximal end and the distal end is stiffer than the proximal end to resist expansion more than the proximal end to prevent migration into the bladder.

7. The balloon catheter of claim 6, wherein the balloon is elongated with a distal end and a proximal end and the proximal end is layered on itself when the bulb is in the unexpanded condition so that during expansion the proximal end of the balloon expand substantially radially with respect to the shaft.

8. The balloon catheter of claim 1, wherein the balloon is elongated with a distal end and a proximal end and the proximal end is layered on itself when the bulb is in the unexpanded condition so that during expansion the proximal end of the balloon expand substantially radially with respect to the shaft.

9. The balloon catheter of claim 1, wherein the flexible shaft includes an outer tube and an inner tube slidable axially inside the outer tube, the distal end of the inner tube extending beyond the distal end of the outer tube, the proximal end of the balloon mounted to an intermediate portion of the outer tube and the distal end of the balloon mounted to the distal portion of the inner tube, so that the balloon can be selectively stretched by relative sliding of the inner tube inside the outer tube.

10. The balloon catheter of claim 1, wherein the maximum diameter of the shaft is less than 26 F.

11. The balloon catheter of claim 1, wherein the maximum diameter of the shaft is about 23.5 to 21 F.

12. The balloon catheter of claim 1, wherein the relative length of the flexible shaft and the length of the viewing lumen is selected with the viewing lumen terminating on the proximal side of the balloon so that when a viewing means is disposed in the viewing lumen and the catheter is in use an operator can view the veru montanum and external sphincter through the viewing means.

13. The balloon catheter of claim 12, wherein the outside of the flexible shaft at a position between the proximal end of the balloon and distal to the distal end of the viewing lumen is provided with graduations visible through a viewing means disposed in the viewing lumen to assist in proper positioning of the balloon.

14. The balloon catheter of claim 1, wherein the balloon is constructed from elastic material selected from the group consisting of polyurethane elastomers with at least one of polyester, nylon and aramid reinforcement, silicone resin with at least one of glass and nylon reinforcement and latex with carbon fiber reinforcement.

15. The balloon catheter of claim 1, wherein the balloon is constructed to expand to at least 30 mm in diameter and to hold about 6 to 8 atm on expansion for at least three expansion/deflation cycles of about 10 minutes in duration.

16. A prostate balloon dilatation catheter for treating benign prostate hyperplasia, comprising:

a flexible catheter shaft flexible along its entire length having a proximal end and a distal end and three lumens therethrough;

the lumens including a first guide wire lumen for receiving a guide wire and the flexible catheter shaft being displaceable along the guidewire, a second inflation lumen through the catheter shaft for providing inflation fluid to the distal region of the catheter shaft and a third viewing lumen through the catheter shaft extending from the proximal end of the shaft to a distal opening before the distal end of the catheter shaft for receiving a viewing telescope;

a catheter tip having a central opening mounted at the distal end of the catheter shaft, the opening communicating with the guide wire lumen;

an expandable balloon mounted at the distal region of the shaft in communication with the inflation lumen for expanding the balloon to dilate the prostate;

the balloon being a flexible expandable member having a distal end and a proximal end, the proximal end of the balloon mounted to an intermediate portion of the shaft and the distal end of the balloon mounted to a distal portion of the catheter;

the proximal end of the balloon being layered on itself to provide a smooth profile when deflated; and the viewing lumen terminating at the proximal side of the balloon for permitting an operator to view through a telescope placed in the viewing lumen the proximal portion of the balloon and anatomical landmarks to dilate the prostate accurately without injury to the external sphincter when the balloon is expanded.

17. The prostate balloon catheter of claim 16, wherein the viewing lumen has a non-circular cross-section and is adapted to receive a telescope and when the telescope is installed in the viewing the lumen the telescope divides the viewing lumen into two separate lumens, one of said separate lumens for providing rinsing fluid to the distal end of the telescope and the other of said lumens for draining the rinsing fluid.

18. A prostate balloon dilatation catheter for treating benign prostate hyperplasia, comprising:

a flexible catheter shaft flexible along its entire length having a proximal end and a distal end;

the shaft having two lumens, the first lumen denominated an inner shaft lumen for receiving an inner flexible shaft, and a second lumen denominated a viewing lumen, the viewing lumen adjacent to the first inner shaft lumen and terminating in a distal opening before the distal end of the catheter shaft for receiving a viewing telescope;

an inner catheter shaft disposed in the first lumen extending from the proximal end of the outer shaft to beyond the distal end of the outer shaft and having a guide wire lumen therethrough;

the inner and outer shafts slidable with respect to each other and an annular space therebetween;

a catheter tip having a central opening mounted at the distal end of the inner catheter shaft, the opening communicating with the guide wire lumen in the inner shaft;

an expandable balloon mounted at the distal region of the catheter shaft with the distal end of the balloon mounted to the distal region of the inner shaft and the proximal end of the balloon mounted to an intermediate region of outer shaft, the annular space between the shafts in communication with the proximal end of the catheter for receiving fluid to expand the balloon for expansion to dilate the prostate;

the balloon being a flexible expandable member providing a smooth profile when deflated due to relative sliding of the shafts; and the viewing lumen in the outer shaft terminating at the proximal side of the balloon for permitting an operator to view through a telescope placed in the viewing lumen the proximal portion of the balloon and anatomical landmarks to dilate the prostate accurately without injury to the external sphincter when the balloon is expanded.

19. The prostate balloon catheter of claim 18, wherein the viewing lumen has a non-circular shape cross-section and is adapted to receive a telescope and when the telescope is inserted forms two separate lumens for providing rinsing fluid to the distal end of the telescope and for removing said fluid.

20. A prostate balloon dilatation catheter for treating benign prostate hyperplasia, comprising:

a flexible shaft which is flexible along its entire length having a proximal end and a distal end and at least three lumens therethrough;

a balloon portion mounted at the distal region of the shaft in communication with one lumen for expanding the balloon to dilate the prostate;

one of the lumens within the flexible shaft being a lumen for receiving a guide wire for assisting and inserting the catheter along the wire, the flexible shaft displaceable along the guide wire;

one of the lumens within the flexible shaft being a viewing lumen having a crescent shape cross-section for receiving viewing means for permitting an operator to view the proximal portion of the balloon and anatomical landmarks to dilate the prostate accurately without injury to the external sphincter when the balloon is expanded; and a telescope disposed with the viewing lumen, the viewing lumen adapted to form two lumens when the telescope is installed, one of the two separate lumens for providing rinsing fluid to the distal end of the telescope and the other of said separate lumens for draining the rinsing fluid.

* * * * *